US012674790B2

(12) United States Patent
Nunes Nogueira et al.

(10) Patent No.: US 12,674,790 B2
(45) Date of Patent: *Jul. 7, 2026

---

(54) UNIVERSAL ELECTRONIC BUNG SYSTEM

(71) Applicant: Watgrid, S.A., Ilhavo (PT)

(72) Inventors: Rogério Nunes Nogueira, Gafanha da Boa Hora (PT); Lúcia Maria Botas Bilro, Gafanha da Encarnação (PT); Fábio Patrício Domingues Gonçalves, Pombal (PT); Pedro Miguel Estima da Costa, Aveiro (PT); Ricardo José Ventura de Sousa e Carvalho Pereira, Oporto (PT)

(73) Assignee: Watgrid, S.A. (PT)

( * ) Notice: Subject to any disclaimer, the term of this patent is extended or adjusted under 35 U.S.C. 154(b) by 198 days.

This patent is subject to a terminal disclaimer.

(21) Appl. No.: 18/515,808

(22) Filed: Nov. 21, 2023

(65) Prior Publication Data

US 2024/0085393 A1 Mar. 14, 2024

Related U.S. Application Data

(63) Continuation of application No. 16/686,547, filed on Nov. 18, 2019, now Pat. No. 11,899,003.

(Continued)

(51) Int. Cl.
*G01N 33/14* (2006.01)
*B65D 90/48* (2006.01)
(Continued)

(52) U.S. Cl.
CPC ........... *G01N 33/146* (2013.01); *B65D 90/48* (2013.01); *C12H 1/22* (2013.01); *G01F 23/80* (2022.01)

(58) Field of Classification Search
CPC .......... G01F 23/80; C12H 1/22; B65D 90/48; G01N 33/146
(Continued)

(56) References Cited

U.S. PATENT DOCUMENTS

| | | | |
|---|---|---|---|
| 4,368,639 A | 1/1983 | Owens | |
| 4,984,451 A | 1/1991 | Wilen | |

(Continued)

FOREIGN PATENT DOCUMENTS

| | | |
|---|---|---|
| CN | 204214506 | 3/2015 |
| EP | 1270716 | 1/2003 |

(Continued)

OTHER PUBLICATIONS

Int'l Search Report and Written Opinion Appln No. PCT/IB2017/053549 mailed Oct. 5, 2017 (6 pgs).

(Continued)

*Primary Examiner* — Nathaniel J Kolb
(74) *Attorney, Agent, or Firm* — McAndrews, Held & Malloy, Ltd.

(57) ABSTRACT

A method and system for monitoring wine in a barrel having a bung hole is provided. The system comprises a sensor enclosure, a sensor conduit, and an original bung. The sensor conduit is operably coupled to the sensor enclosure. The original bung comprises a passage hole for inserting the sensor conduit through the original bung. The original bung also comprises a space for inserting at least a portion of the sensor enclosure. This space does not extend through the original bung. The outer diameter of the original bung is determined by the diameter of the bung hole of the barrel.

10 Claims, 8 Drawing Sheets

Enclosure 201

Sensor Device 100

Sensor Conduit 305

Sensor Conduit 303

Related U.S. Application Data

(60) Provisional application No. 62/769,645, filed on Nov. 20, 2018.

(51) Int. Cl.
  *C12H 1/22* (2006.01)
  *G01F 23/80* (2022.01)

(58) Field of Classification Search
  USPC .......................................................... 73/431
  See application file for complete search history.

(56) References Cited

U.S. PATENT DOCUMENTS

| | | | | | |
|---|---|---|---|---|---|
| 5,546,804 | A | * | 8/1996 | Johnson ................. | H05K 5/069 |
| | | | | | 73/431 |
| 5,953,954 | A | | 9/1999 | Drain | |
| 6,539,819 | B1 | * | 4/2003 | Dreyer ................ | G01F 23/2967 |
| | | | | | 73/431 |
| 7,659,980 | B1 | * | 2/2010 | Mitchell ................ | G01N 21/53 |
| | | | | | 356/338 |
| 2004/0076946 | A1 | | 4/2004 | Trauner | |
| 2014/0081580 | A1 | * | 3/2014 | Kim ................... | G01N 33/0004 |
| | | | | | 702/24 |
| 2015/0198474 | A1 | | 7/2015 | Howard | |
| 2018/0136020 | A1 | * | 5/2018 | Sweet ..................... | H04L 67/10 |

FOREIGN PATENT DOCUMENTS

| | | | | | |
|---|---|---|---|---|---|
| EP | 1462776 | A1 | * | 9/2004 | ............. G01F 23/74 |
| GB | 2259974 | A | * | 3/1993 | ............. B22D 1/005 |
| WO | 2013028144 | A3 | | 2/2013 | |
| WO | 2017216746 | | | 12/2017 | |
| WO | 2020/104850 | A1 | | 5/2020 | |

OTHER PUBLICATIONS

N. Oliveiram et al., Winegrid®: the remote and real-time wine production process monitoring system (6 pgs).

Portuguese Search Report Appln No. 109451 dated Nov. 18, 2016 (2 pgs).

Int'l Search Report and Written Opinion Appln No. PCT/IB2019/001251 mailed Apr. 8, 2020.

Int'l Preliminary Report on Patentability Appln No. PCT/IB2019/001251 mailed Jun. 3, 2021.

Australian Examination Report No. 1 Appln No. 2019382977 dated May 5, 2022.

Australian Examination Report No. 2 Appln No. 2019382977 dated Jan. 10, 2023.

Australian Examination Report No. 3 Appln No. 2019382977 dated Apr. 19, 2023.

About—Sapere Liquid Knowledge [retrieved from internet on Apr. 18, 2023] < URL: https://web.archive.org/web/20180827112553/http:/sapereliquidknowledge.com/index.php/about-us/ Published on Aug. 27, 2018 as per Wayback Machine.

Di Gennaro, S. F., et al. 'Wireless real-time monitoring of malolactic fermentation in wine barrels: the Wireless Sensor Bung system', Australian Journal of Grape and Wine Research, Dec. 21, 2012, vol. 19, Issue 1, pp. 20-24.

Di Gennaro, S. F., et al., 'An Open-Source and Low-Cost Monitoring System for Precision Enology', Sensors, Dec. 5, 2014, vol. 14, Issue 12, pp. 23388-23397.

European Office Communication Appln No. 19842397.2 dated Apr. 8, 2024.

Australian Examination Report No. 1 Appln No. 2023202797 dated Jan. 24, 2025.

Lasky, Michael S. "Monitor Barrels Anywhere with Wireless Smart Bungs" WineBusiness Monthly. Published Feb. 1, 2017 URL: https://www.winebusiness.com/wbm/article/179536.

* cited by examiner

100

Enclosure 201

Sensor Device 100

Sensor Conduit 305

Sensor Conduit 303

Enclosure 201

Power Button & Alarm LED 203

Sensor Conduit 305

Sensor Conduit 303

Bung 307
Top View

Passage for
Sensor Conduit
501

Space for
Sensor Enclosure
503

Bung 307
Side View

Space for
Sensor Enclosure
503

Passage for
Sensor Conduit
501

Bung 307
Bottom View

Passage for
Sensor Conduit
501

Enclosures
201

Barrel
601

Bung
307

Enclosure
201

Wine

Sensor
Conduit
303

UNIVERSAL ELECTRONIC BUNG SYSTEM

PRIORITY CLAIM

This patent application is a continuation of patent application Ser. No. 16/686,547 filed on Nov. 18, 2019, which claims the benefit of priority to U.S. provisional patent application 62/769,645 filed on Nov. 20, 2018, now expired. The aforementioned documents are hereby incorporated herein by reference in their entirety.

BACKGROUND

Limitations and disadvantages of conventional and traditional monitoring systems for winemaking will become apparent to one of skill in the art, through comparison of such systems with some aspects of the present invention as set forth in the remainder of the present application with reference to the drawings.

BRIEF SUMMARY OF THE INVENTION

Monitoring systems for winemaking substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

This disclosure describes systems for monitoring winemaking or other similar processes, for example. Many facets of wine change during the processes of maceration, fermentation and maturation. Parameters (e.g., pressure, temperature, density, distance, level, turbidity, color, pH, alcohol content) may be automatically captured continuously, periodically or otherwise over time and wirelessly transferred to a database for analysis and storage. Thresholds may be set such that a winemaker can be notified when the monitored parameters are out of a selected or desired range.

Figure 1:
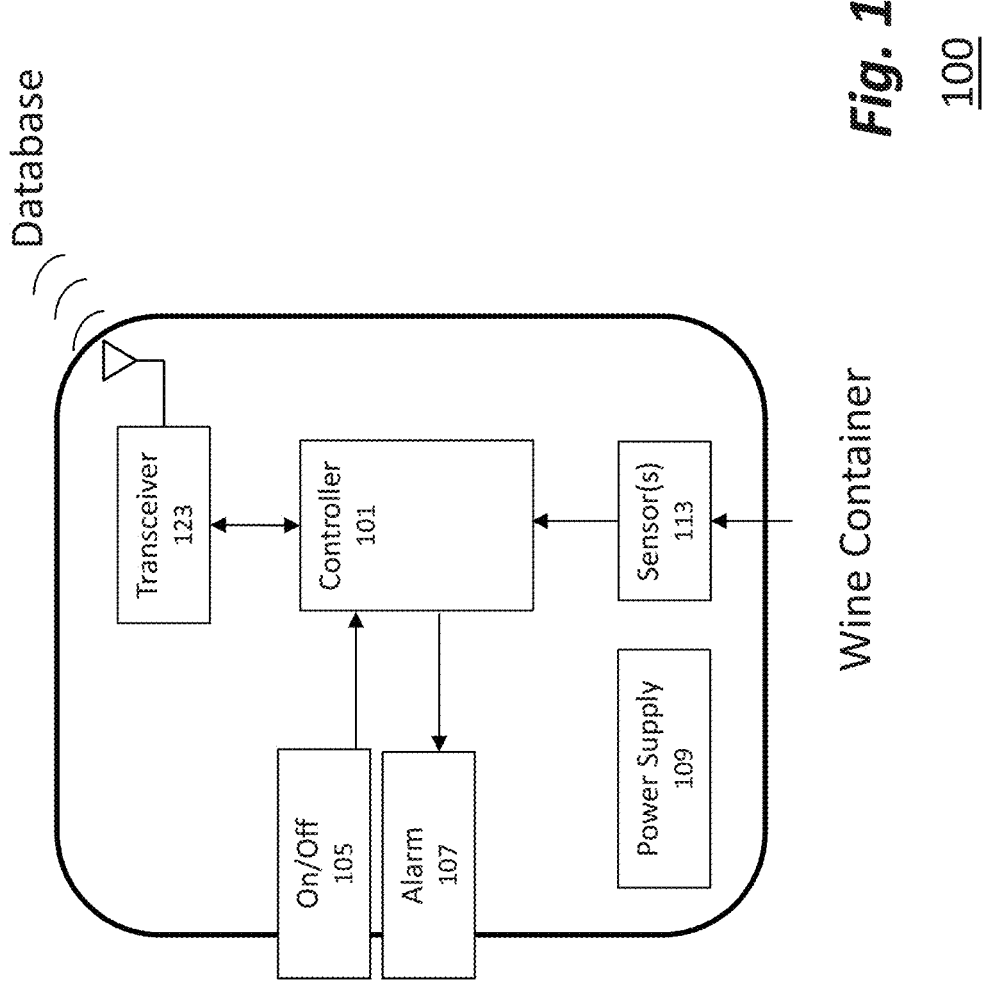
FIG. 1 illustrates components of a sensor device in accordance with an example implementation of this disclosure.

FIG. 1 illustrates components of a sensor device 100 in accordance with an example implementation of this disclosure. The depicted components of the sensor device 100 include a controller 101, an on/off switch 105, an alarm 107, a power supply 109, one or more sensor(s) 113, and a transceiver 123.

In In operation, in a winemaking example, the sensor device 100 is coupled to a wine barrel or vat during a winemaking process. The one or more sensor(s) 113 may measure the temperature of the wine, and the one or more sensor(s) 113 measure additional parameters (e.g., pressure, density, distance, level, turbidity, color, pH, alcohol content) of the wine. These measurements are conveyed to the controller 101, which is operable to control a wireless transmission of the information, via transceiver 123, to a database for analysis and storage. Analysis of this information in the database may be performed by a remote device on the network. The transceiver 123 may use Bluetooth, WiFi, LoRa and/or any digital cellular standard. The sensor communicates with our computational platform built in a cloud based virtual machine.

The controller 101 may be operable to derive certain parameters from those supplied by the one or more sensor(s) 113. For example, a wine level may be derived according to a pressure or distance measurement. If the power supply 109 comprises one or more batteries, for example, the microcontroller 101 may be operable to monitor and report to the database when the batteries should be replaced or recharged.

The on/off switch 105 may comprise a button. Pressing the button 105 ON can trigger the sensor device 100 to send a beacon to enable pairing with a network. Pressing the button 105 OFF can trigger the sensor device 100 to store all current information in a Flash card before powering down. Button 105 may also be a non-touch capacitive button.

The sensor device 100 may generate local alarms. The alarm 107 may convey a visual and/or an audio alarm 107. Different sounds and/or different colors may indicate various conditions. A flashing red light or a beeping may indicate a low battery. A solid yellow light may indicate a low wine level and a need for topping off the wine. A solid blue light may indicate that the wine is below a low temperature threshold. The alarm 107 may comprise an LED. Such an LED may be incorporated into an on/off button 105. The alarm 107 may also be used to indicate the status of a pairing of the sensor device 100 to a local network.

The one or more sensor(s) 113 are operably coupled to a wine container, such as a barrel or a vat. The type of sensors used may depend of the current stage of winemaking. During maturation, for example, a pressure sensor may be used to measure a change in wine level. A distance sensor, based on time-of-flight measurements may also be used.

Figure 2:
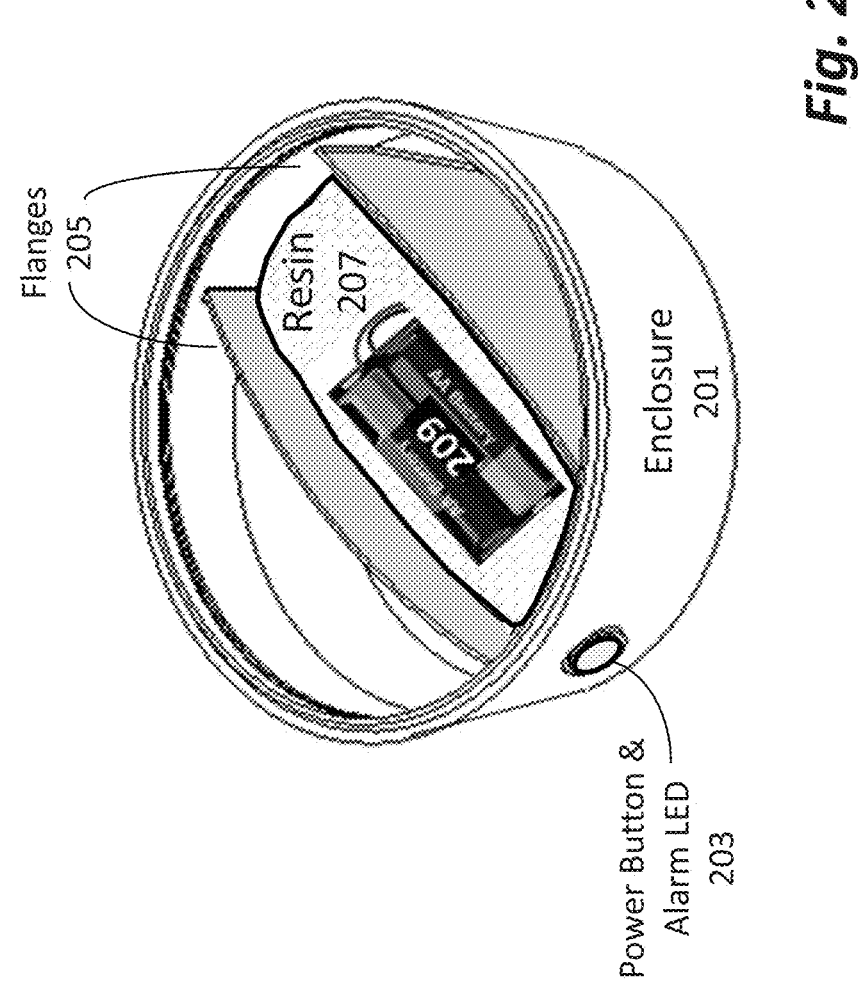
FIG. 2 illustrates an enclosure for a sensor device in a sensor system in accordance with an example implementation of this disclosure.

FIG. 2 illustrates an enclosure 201 for a sensor device 100 (as described regarding FIG. 1) in a sensor system in accordance with an example implementation of this disclosure. The enclosure comprises an LED incorporated into an on/off button 203 to provide an alarm as well as power control. The electronic circuitry (i.e., controller 101, sensor(s) 113 and transceiver 123 as described regarding FIG. 1) and an antenna may be mounted in the enclosure 201 and encased in resin 207 for durability and to protect from moisture. The resin area 207 may also be limited by flanges 205. Batteries 209 are accessible above the resin 207 to enable replacement by a user. The batteries may be, for example, AA, AAA or and other size.

Figure 3B:
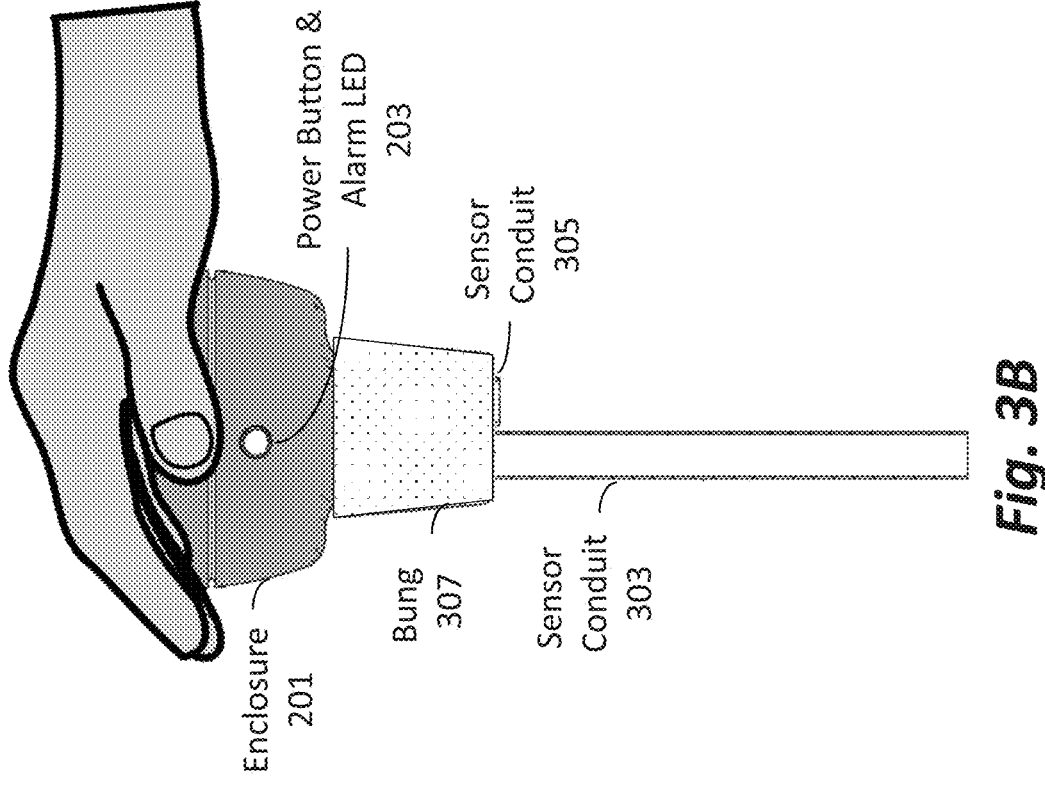
FIG. 3B illustrates a sensor system comprising a sensor device and a removable bung in accordance with an example implementation of this disclosure.
Figure 3A:
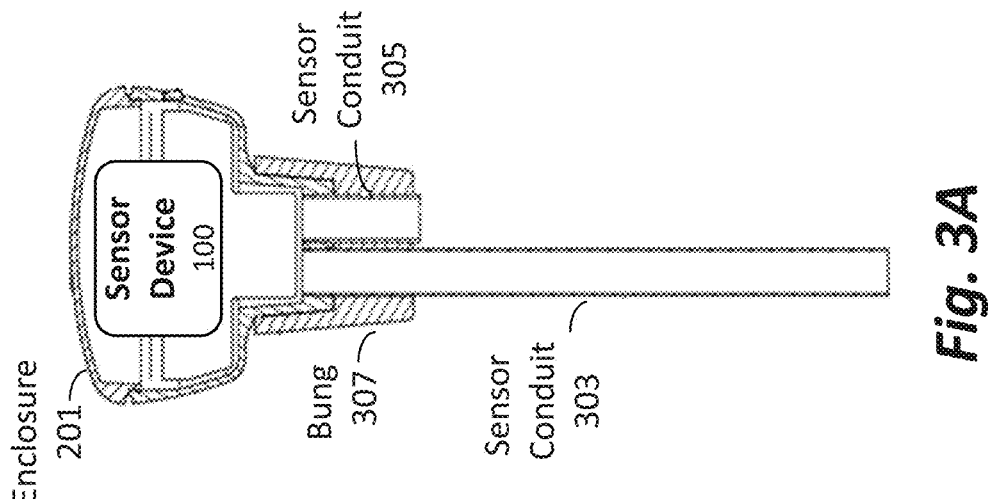
FIG. 3A illustrates a cut-away view of a sensor system comprising a sensor device and a removable bung in accordance with an example implementation of this disclosure.

FIG. 3A illustrates a cut-away view of a sensor system comprising a sensor device 100 in accordance with an example implementation of this disclosure. The depicted components of the sensor system include the sensor device 100 in an enclosure 201, one or more sensor conduits 303 and/or 305, and a replaceable bung 307. In a sensor system with one sensor conduit 303, for example, sensor conduit 305 would not exist. The enclosure 201 may be made of flexible plastic or hard rubber. The sensor conduits 303 and 305 may be stainless steel. The bung 307 may be made of silicone.

FIG. 3B illustrates an external view of the same sensor system as shown FIG. 3A. The enclosure 201 is ergonomically designed to fit a human hand to aid installation and removal. Accordingly, an example diameter of the enclosure 201 is 3½ to 4½ inches (90 to 115 mm).

The bung 307 can be interchanged without affecting the rest of the sensor system. For example, the bung 307 may deteriorate over time. Replacement of a silicone bung 307 is more cost effective than replacing the entire sensor system. Also, different barrels may have different sized bung holes. Replacing the silicone bung 307 allows a winemaker to use the same monitor regardless of the barrel or the size of the bung hole.

Figure 4B:
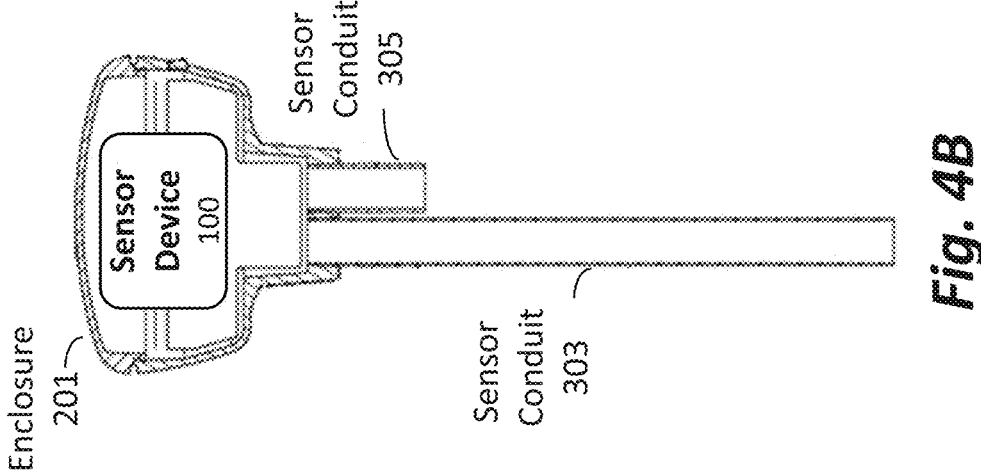
FIG. 4B illustrates a cut-away view of a sensor system comprising a sensor device in accordance with an example implementation of this disclosure.
Figure 4A:
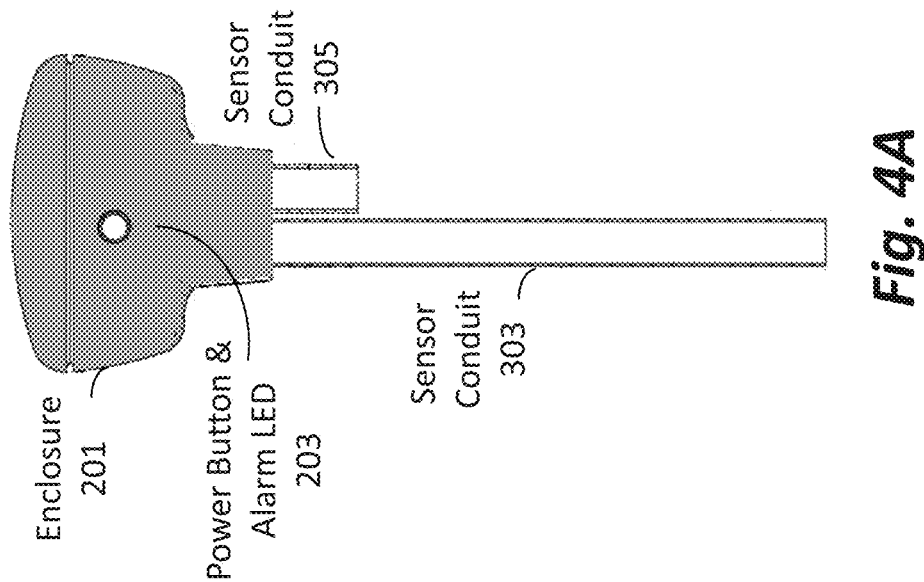
FIG. 4A illustrates a sensor system comprising a sensor device in accordance with an example implementation of this disclosure.

FIG. 4A illustrates an external view of the same sensor system as shown FIGS. 3A and 3B when the bung 307 is removed. FIG. 4B illustrates a cut-away view of the same sensor system as shown FIG. 4A.

Figures 5A, 5B, 5C:
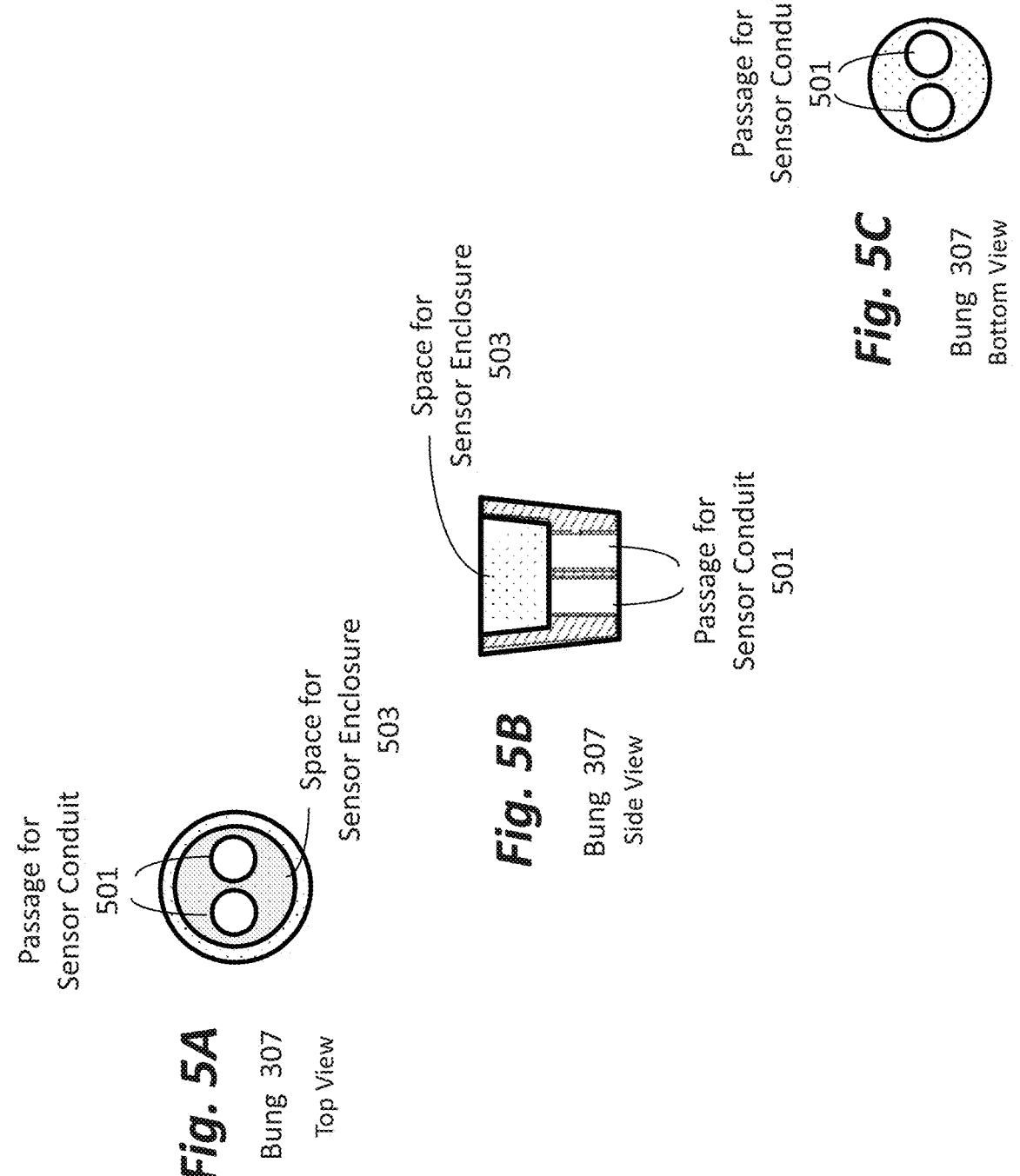
FIG. 5A illustrates a top view of a removable bung in accordance with an example implementation of this disclosure.
FIG. 5B illustrates a cut-away side view of a removable bung in accordance with an example implementation of this disclosure.
FIG. 5C illustrates a bottom view of a removable bung in accordance with an example implementation of this disclosure.

FIG. 5A illustrates a top view of the removable bung 307. FIG. 5B illustrates a cut-away side view of the removable bung 307. FIG. 5C illustrates a bottom view of the removable bung 307. A sensor system may comprise one or more sensor conduits 303 and 305. Accordingly, the bung 307 has a passage hole for each of the one or more sensor conduits 303 and 305. Additionally, the bung 307 may fit around the sensor enclosure 201. A space 503 for the sensor enclosure 201 is provided from the top of the bung 307.

Figures 6A, 6B:
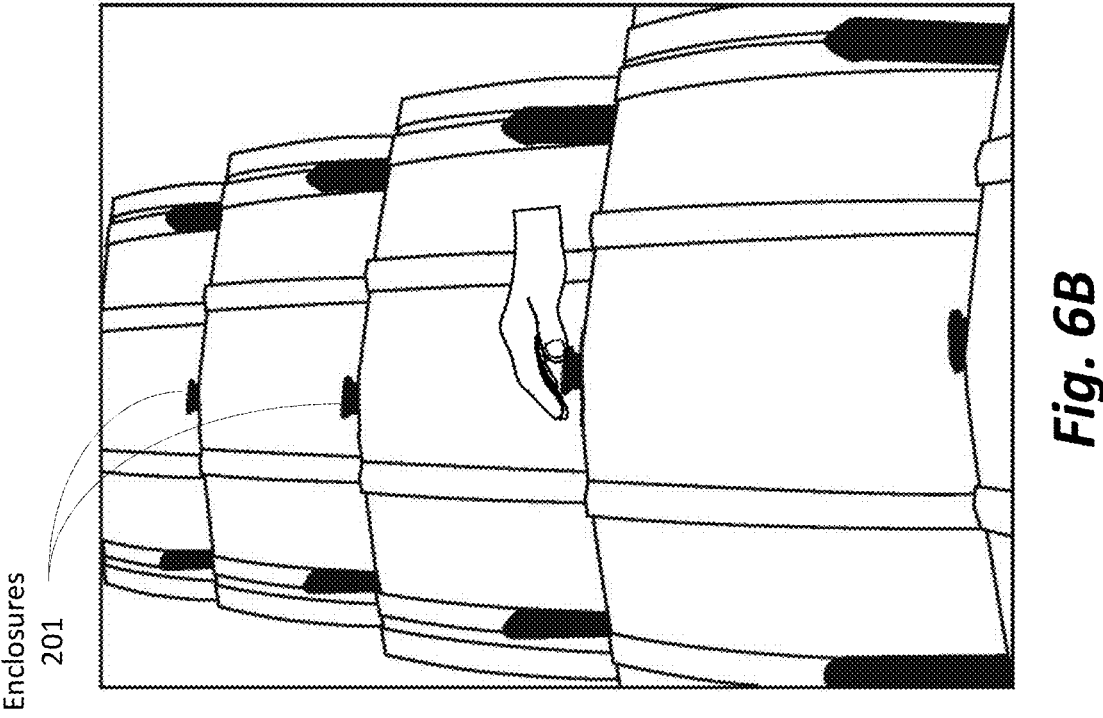
FIG. 6A illustrates a cut-away side view of a sensor system in a wine barrel in accordance with an example implementation of this disclosure.
FIG. 6B illustrates a top view of sensor systems in wine barrels in accordance with an example implementation of this disclosure.

FIG. 6A illustrates a cut-away side view of a sensor system in a wine barrel 601. The sensor system is inserted into the barrel 601 and held in place by the bung 307. One or more sensor conduits 303 and 305 are in contact with the wine. One or more sensor conduits 303 and 305 within the bung 307 are in contact with the space above the wine. Only the sensor device enclosure 201 and partially the bung 307 are visible from the outside of the wine barrel 601.

FIG. 6B illustrates a top view of a plurality of sensor systems in wine barrels.

Figure 7:
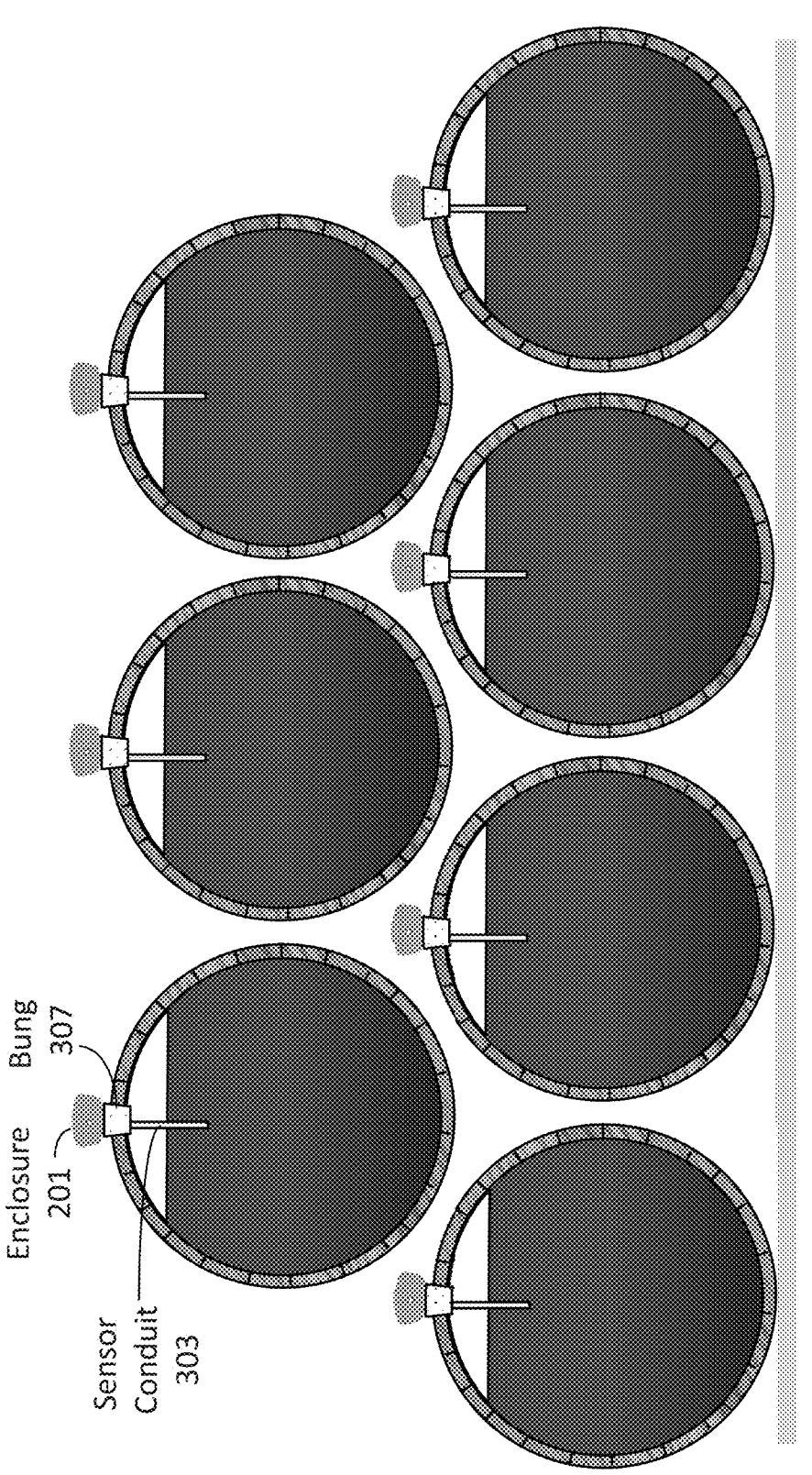
FIG. 7 illustrates a cut-away side view of sensor systems in stacked wine barrels in accordance with an example implementation of this disclosure.

FIG. 7 illustrates a cut-away side view of the sensor systems in stacked wine barrels. A sensor system is inserted into each barrel and held in place by the bung 307. One or more sensor conduits 303 and 305 are in contact with the wine in each barrel.

Figure 8:
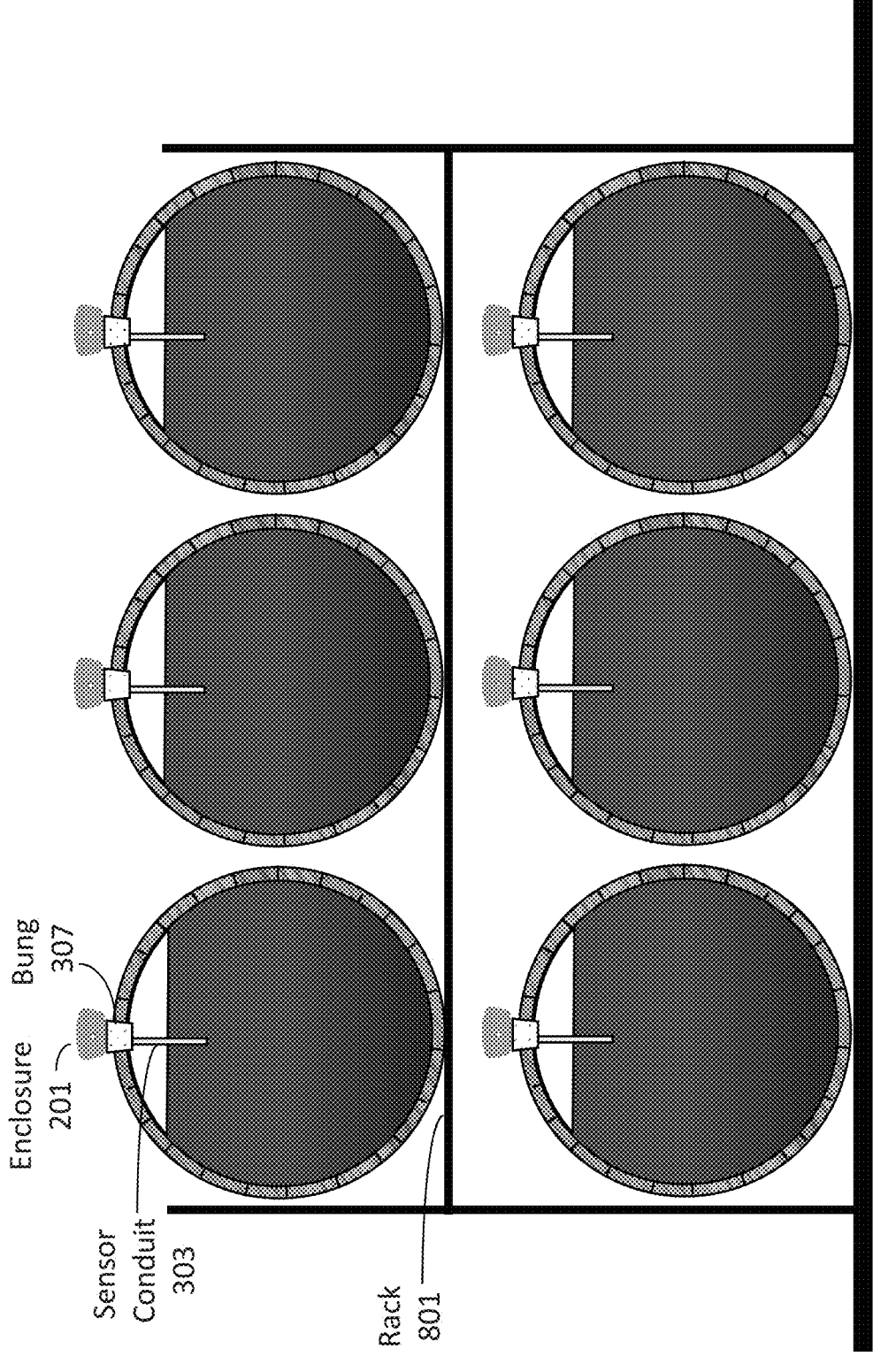
FIG. 8 illustrates a cut-away side view of sensor systems in racked wine barrels in accordance with an example implementation of this disclosure.

FIG. 8 illustrates a cut-away side view of sensor systems in racked wine barrels. A sensor system is inserted into each barrel and held in place by the bung 307. One or more sensor conduits 303 are in contact with the wine in each barrel. The sensor device enclosure 201 is short enough to fit under the rack 801.

The enclosure 201 is designed to allow wine barrels to be stacked as illustrated in FIG. 7 or racked as illustrated in FIG. 8. Accordingly, an example height of the enclosure 201 is less than 2½ inches (64 mm).

A system (e.g., FIGS. 3A, 3B, 4A and 4B) for monitoring wine in a barrel having a bung hole is provided. The system comprises a sensor enclosure (e.g., 201), one or more sensor conduits (e.g., 303, 305), and an original bung (e.g., 307). One or more sensor conduits (e.g., 303, 305) are operably coupled to the sensor enclosure (e.g., 201). The sensor conduits (e.g., 303, 305) may also be detached from the sensor enclosure (e.g., 201) temporarily for cleaning procedures. The original bung (e.g., FIGS. 5A, 5B and 5C) comprises one or more passage holes (e.g., 501) for inserting the sensor conduit (e.g., 303, 305) through the original bung (e.g., 307). In a sensor system with one sensor conduit 303, for example, the passage for the sensor conduit 501 would only have one hole. The original bung (e.g., 307) also comprises a space (e.g., 503) for inserting at least a portion of the sensor enclosure (e.g., 201). This space (e.g., 503) does not extend through the original bung. The outer diameter of the original bung is determined by the diameter of the bung hole of the barrel.

The original bung may be interchanged with an alternative bung that has an outer diameter that may or may not be a different size. Such interchangeability allows the winemaker to use barrels with different bung hole sizes, while not requiring the extra time and expense of a new sensor conduit (e.g., 303, 305) and new enclosure (e.g., 201) with new sensor electronics. Such interchangeability also allows the winemaker to reuse the sensor conduit (e.g., 303, 305) and the enclosure (e.g., 201) even after the original bung has worn out.

As shown in FIG. 1, the sensor enclosure (e.g., 201) may comprise a power supply (e.g., 109) and a controller (e.g., 101). The controller (e.g., 101) is also able to wirelessly communicate with a remote database via the transceiver (e.g., 123).

The controller (e.g., 101) may be encased in a resin (e.g., 207 of FIG. 2), while the power supply (e.g., 109) remains accessible above the resin (e.g., 207). Such encasement provides protection to the controller (e.g., 101) from, for example, water and misuse. The resin (e.g., 207) may fill a volume between two flanges (e.g., 205) within the sensor enclosure (e.g., 201). An antenna, operably coupled to the controller (e.g., 101) and transceiver (e.g., 123) is may be located on the surface of one of the two flanges (e.g., 205).

An outer dimension across the sensor enclosure (e.g., 201) may be 3½ to 4½ inches to allow the winemaker to grasp the sensor enclosure as illustrated in FIG. 3B. The height of the sensor enclosure may be less than 2½ inches to allow the wine barrels to be stacked as illustrated in FIG. 7 and/or racked as illustrated in FIG. 8.

The aforementioned system enables the winemaker to monitor the wine by inserting a sensor conduit (e.g., 303 and/or 305) through one or more passage holes (e.g., 501) in an original bung (e.g., 307); inserting the sensor enclosure (e.g., 201) into the original bung (e.g., 307); and inserting the original bung (e.g., 307) into the bung hole of the original barrel.

The winemaker can also swap bungs by removing the original bung (e.g., 307) from the bung hole of the barrel; removing the original bung (e.g., 307) from the sensor enclosure (e.g., 201) and the sensor conduit (e.g., 303 and/or 305); inserting the sensor conduit (e.g., 303 and/or 305) through a passage hole in an alternative bung; inserting the sensor enclosure (e.g., 201) into the alternative bung; and inserting the alternative bung into a bung hole of an alternative barrel.

As utilized herein the terms "circuits" and "circuitry" refer to physical electronic components (i.e. hardware) and any software and/or firmware ("code") which may configure the hardware, be executed by the hardware, and or otherwise be associated with the hardware. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

The present invention may be realized in hardware, software, or a combination of hardware and software. The present invention may be realized in a centralized fashion in at least one computing system or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

The present invention may be realized in a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

While the present invention has been described with reference to certain embodiments, it will be understood by those skilled in the art that various changes may be made and equivalents may be substituted without departing from the scope of the present invention. Those skilled in the art will understand that, in addition to winemaking, the present invention may be used for making of other products (e.g., whiskey, cognac, brandy, rum, gin, vodka, tequila, beer) without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system, wherein the system comprises:
   a bung configured to be inserted into a bung hole of a barrel, wherein:
      the bung is a conical frustum comprising a larger circular side and a smaller circular side,
      a passage hole extends through the bung between the larger circular side of the conical frustum and the smaller circular side of the conical frustum,
      the larger circular side of the conical frustum and the smaller circular side of the conical frustum are determined by a diameter of the bung hole of the barrel,
      the larger circular side of the conical frustum comprises a space,
      the space is wider than the passage hole, and
      the space does not extend through the bung;
   a sensor enclosure, wherein:
      the sensor enclosure is configured to surround a sensor device,
      at least a portion of the sensor enclosure is located in the space of the bung,
      the sensor device is located above the bung, and
      the bung is configured to be separable from the sensor enclosure; and
   a sensor conduit operably coupled to the sensor enclosure, wherein:
      the sensor conduit is inserted through the passage hole of the bung.

2. The system according to claim 1, wherein:
   the sensor enclosure comprises a power supply and a controller, and
   the controller is operable to wireless communicate with a remote database.

3. The system according to claim 2, wherein:
   the controller is encased in a resin, and
   the power supply is accessible above the resin.

4. The system according to claim 3, wherein the resin fills a volume between two flanges within the sensor enclosure.

5. The system according to claim 4, wherein
   an antenna is located on the surface of one of the two flanges, and
   the antenna is operably coupled to the controller.

6. The system according to claim 1, wherein an outer dimension across the sensor enclosure is 3 ½ to 4 ½ inches.

7. The system according to claim 1, wherein a height of the sensor enclosure is less than 2 ½ inches.

8. The system according to claim 1, wherein the system comprises the barrel.

9. A system, wherein the system comprises:
   a bung configured to be inserted into a bung hole of a barrel, wherein:
      the bung is a conical frustum comprising a larger circular side and a smaller circular side,
      a passage hole extends through the bung between the larger circular side of the conical frustum and the smaller circular side of the conical frustum,
      the larger circular side of the conical frustum and the smaller circular side of the conical frustum are determined by a diameter of the bung hole of the barrel,
      the larger circular side of the conical frustum comprises a space,
      the space is wider than the passage hole, and the space does not extend through the bung;
a sensor enclosure, wherein:
    the sensor enclosure is configured to surround a sensor
      device,
    at least a portion of the sensor enclosure is located in
      the space of the bung, and
    the bung is configured to be separable from the sensor
      enclosure;
a sensor conduit operably coupled to the sensor enclosure,
    wherein:
    the sensor conduit is inserted through the passage hole
      of the bung; and
an alternative bung, wherein:
    the bung is interchangeable with the alternative bung.

10. The system according to claim 9, wherein:
the bung and the alternative bung have the same dimen-
    sions.

\* \* \* \* \*